United States Patent [19]
Fendler et al.

[11] 4,372,312
[45] Feb. 8, 1983

[54] ABSORBENT PAD INCLUDING A MICROFIBROUS WEB

[75] Inventors: Eleanor J. Fendler; Leo J. Bernardin, both of Appleton, Wis.

[73] Assignee: Kimberly-Clark Corporation, Neenah, Wis.

[21] Appl. No.: 266,795

[22] Filed: May 26, 1981

[51] Int. Cl.³ .............................................. A61F 13/16
[52] U.S. Cl. ................................................ 128/290 R
[58] Field of Search ............... 128/284, 286, 287, 288, 128/290 R, 290 W, 296

[56] References Cited
U.S. PATENT DOCUMENTS

| | | | |
|---|---|---|---|
| 3,371,667 | 3/1968 | Morse | 128/290 R |
| 3,525,338 | 8/1970 | Bernadin | 128/290 R |
| 4,023,571 | 5/1977 | Comerford et al. | 128/290 R |
| 4,100,324 | 7/1978 | Anderson et al. | 128/290 W |

*Primary Examiner*—C. Fred Rosenbaum
*Attorney, Agent, or Firm*—Howard Olevsky; William D. Herrick

[57] ABSTRACT

An absorbent pad containing a nonwoven hydrophilic thermoplastic filamentary microfibrous web as part of the absorbent material is provided. The microfibrous web exhibits good wicking and fluid retention properties.

10 Claims, 5 Drawing Figures

ABSORBENT PAD INCLUDING A MICROFIBROUS WEB

FIELD OF THE INVENTION

This invention relates to an absorbent pad and particularly to pads designed to absorb blood containing biological fluids.

BACKGROUND OF THE INVENTION

One of the problems with sanitary appliances such as tampons, surgical dressings, sanitary napkins and the like is that when conventional absorbent material is used the products resulting are bulky and uncomfortable. Another problem, one which is particularly acute with tampons and sanitary napkins, is that when conventional absorbent materials are used they are not used efficiently. In many sanitary napkins substantial portions of the absorbent layer are not used at all.

One of the attempts at solving the problems associated with the sanitary napkin underutilization is disclosed in U.S. Pat. No. 3,525,338 issued to Leo J. Bernardin. This patent discloses utilizing a layer of glass microfiber as part of the absorbent material. The glass microfibrous layer has good absorbent capacity and wicking capabilities. When a layer of glass microfiber is deposited horizontally between two layers of conventional absorbent material, the absorbent capacity of the napkin is increased as well as the efficiency, the latter due to the lateral wicking properties of the glass microfiber layer. The fluid transfer along the surface and through the interstices of the microfibrous mat allows for good fluid distribution in areas distal from the initial fluid contact.

While the absorptive and wicking capabilities of glass microfiber webs are highly desirable, the commercial utilization of glass microfiber is difficult because of the lack of integrity of the glass microfiber mat. This lack of integrity led, at times, to disintegration of the mat during use and problems in machinability during the napkin manufacturing process. The comparatively high cost of the glass microfiber compared to conventional absorbent material was also a drawback.

While other kinds of microfibers are known such as those described in "'Superfine Thermoplastic Fibers' appearing in Industrial and Engineering Chemistry, Volume 48, Number 8, pages 1342–1346 which describes work done at the Naval Research Laboratories in Washington, D.C. (also see Naval Research Laboratory Report 111437 dated Apr. 15, 1954, and U.S. Pat. No. 3,676,242, issued July 11, 1972, to Prentice)", the art has looked upon these thermoplastic microfibers as inimical to absorption of aqueous solutions. In the medical field, such microfibers have been used as a blood filter. The fibers act to restrain the blood cells while allowing fluid to pass through. This is due to the treatment of the microfibrous web rendering it more hydrophilic than the untreated web. This is traditionally done with wetting agents or surfactants.

The hydrophobicity of this material is so well known that U.S. Pat. No. 4,059,114 directed to a thin panty shield type of sanitary napkin discloses utilizing the meltblown microfibers as a fluid impermeable baffle.

SUMMARY OF THE INVENTION

According to this invention, surprisingly, microfibrous webs which have been rendered increasingly hydrophilic by suitable surface treatment have been found to have fluid transfer and wicking properties similar to glass microfibrous webs and, are therefore suitable as an absorbent component in sanitary appliances. While the sanitary appliance featuring an absorbent containing a nonwoven hydrophobic thermoplastic filamentary microfibrous web which has been rendered increasingly hydrophilic has a variety of uses according to the teachings of this invention, it is particularly useful as a component in a sanitary napkin. For purposes of this invention microfiber or microfibrous refers to a fiber or filament wit an average diameter less than 15 microns and preferably less 12 microns. If a web formed from these materials is discontinuous i.e. made up of a plurality of fibrils or fibers, then these should be at least 50% of the fibers existing as microfibers to fall within the definition of this invention.

BRIEF DESCRIPTION OF THE DRAWINGS

This invention can better be understood by reference to the drawings in which.

Figure 4:
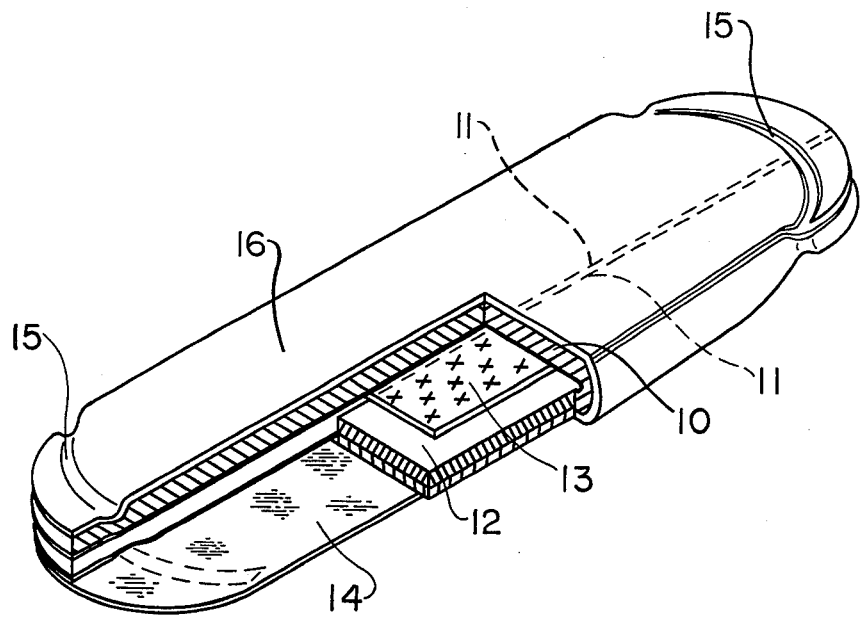
Figure 5:
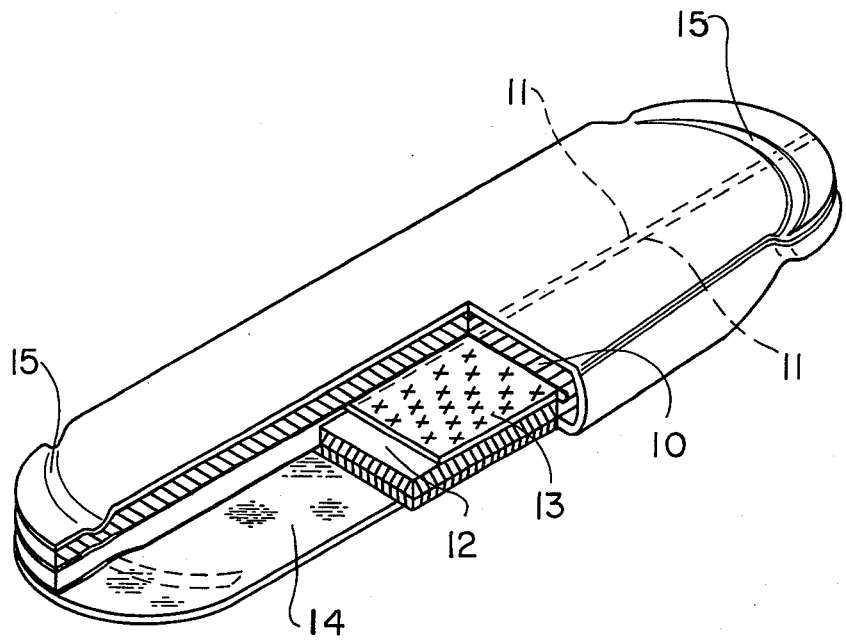

In all the figures like numbers denominate like parts. As can be seen in FIGS. 4 and 5 an absorbent layer 10 containing fusible fibers is surrounded by a fluid permeable wrap 16 and is folded underneath itself to form closely adjacent edges shown in phantom lines 11. An intermediate absorbent layer of nonwoven microfibers is positioned generally in the center of the absorbent matrix resting upon the top of the folded surface 12 of the absorbent material 10 and a fluid impermeable baffle 14 is adhesively attached to the bottom of the folded absorbent layer. The transverse ends of the abosrbent layer 10 are not sealed at the edges but instead are sealed by fusing. This fusing generally appears in the absorbent material as clear this semicircular bands 15 which are inset from the napkin ends. By leaving the extreme ends of the napkin unattached a loose flexible end results which is more comfortable than an end which is bonded to the very edge.

FIG. 5 is identical to FIG. 4 except that the microfibrous web 13 extends and conforms to the folded edge of the abosrbent material layer 10.

Figure 1:
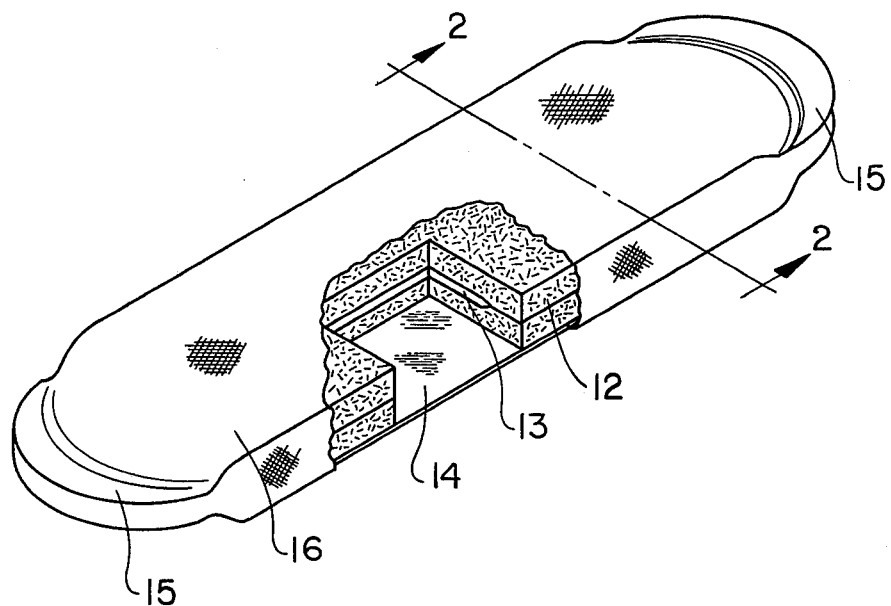
FIG. 1 is a perspective view of a sanitary napkin according to this invention.
Figure 2:
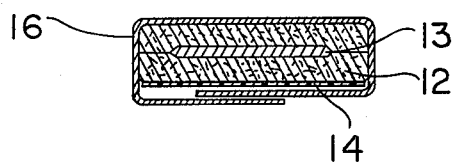
FIG. 2 is a cross sectional view taken along the lines 2—2 of FIG. 1.
Figure 3:
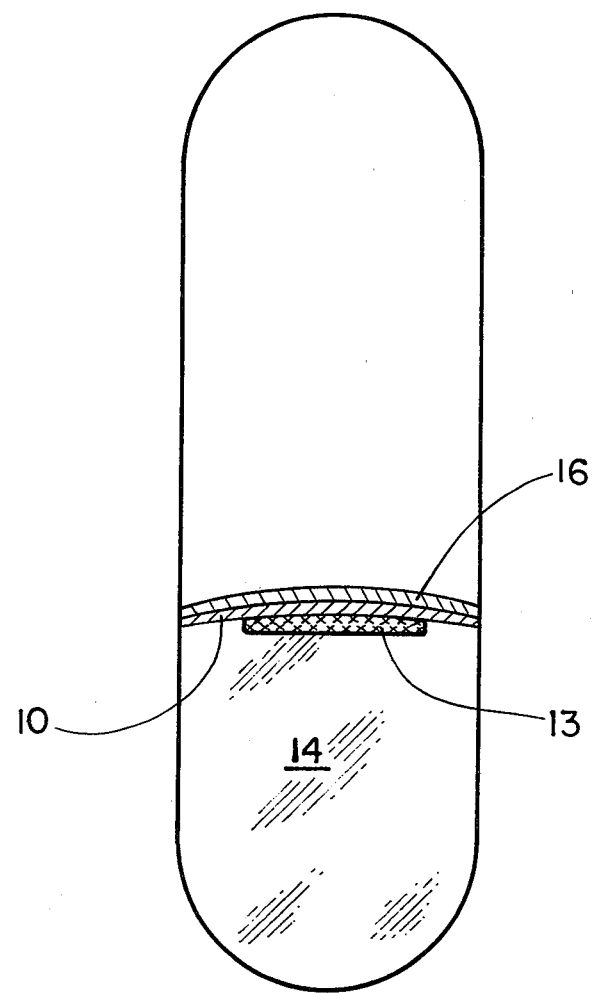
FIG. 3 is a plan view partially in cross section of a panty liner according to this invention and FIGS. 4 and 5 are perspective views partially in cross section showing sanitary napkins having longitudinally folded edges with microfibrous inserts according to the teachings of this invention.

FIGS. 1 and 2 depict a conventional full size napkin in which the microfibrous web is located between two absorbent layers. The top absorbent layer is one which should have capillary attraction which is less than that of the microfibrous web in order to draw fluid through the top layer. The larger the differential in capillary attaraction the more rapidly the fluid will be drawn through the layer and, as a concomitant benefit, the drier the cover material due to the seed with which the fluid is removed.

Surprisingly, the microfibrous web according to this invention can be used in a panty liner such as that described in U.S. Pat. No. 3,881,490. The microfibrous web can either be coterminous with the ends of the absorbent material or can be slightly inset. If the web is coterminous, it is desired that the web be subjected to fusing to form a barrier at or near the periphery of the pad. This fusing of the web to the absorbent material presupposes the utilization of thermoplastic in the absorbent layer. This is indeed a preferred embodiment and will be discussed in more detail subsequently. In any event if fusing can be accomplished in the area around the periphery of the pad the possibility of side staining i.e. fluid runoff beyond the peripheral portions of the pad is substantially reduced.

DETAILED DESCRIPTION OF THE INVENTION

The microfibrous web of this invention, as mentioned above, performs fluid transfer, fluid wicking and fluid absorption functions which would not ordinarily be expected of this type of material. The wetting of this conventionally hydrophobic material is accomplished by treatment with suitabl medically safe surfactants examples of which are of the following types: sodium alkyl sulfosuccinates; polyoxyethylene alkanols, phenols, and sorbitan esters of $C_{12}13$ $C_2O$ fatty acids; alkylammonium alkyl sulfates and mixtures of the above with the anionic and/or nonionic surfactants generally preferred. The wetting agents are present at a level of 0.1 to 5.0% by weight of the fibers preferred with a range of 0.5 to 3.0% especially preferred depending on the wetting agent chosen, while bearing in mind that lowver fiber diameter increases capillary attraction, wicking and fluid retention. Of course, excess levels of wetting agents may be used but there is little gain in performance above the 5% level.

In all of the embodiments depicted in the drawings, it is preferred that at least some of the other absorbent material contain fusible fibers. The fusible fibers promote sealing by fusing to the baffle and/or the microfibrous layer itself. Particularly preferred is a mat which is made of coformed material. This coformed material is described in U.S. Pat. No. 4,100,324. This nonwoven material has a fabric-like finish and is made up of an airformed matrix of thermoplastic polymeric fibers having an average diameter of less than about 10 microns i.e. this diameter is in the microfiber range and a multiplicity of individualized wood pulp fibers dispersed throughout the matrix and serving to space these microfibers from each other. The material is formed by initially utilizing a primary air stream with the meltblown microfibers and the secondary air stream containing wood pulp fibers and merging the two under turbulent conditions and subsequently the integrated air stream along a forming surface. The fabric-like appearance of this material provides a visually appealing absorbent. Also inherent in the coformed material is increased resiliency when compared to conventional cellulosic absorbents. The inclusion of fusible fiber while having the advantages previously indicated does reduce the absorbency of the coformed mat. The inclusion of a layer of microfibrous thermoplastic web, however, in conjunction with coformed material produces a sanitary napkin having superior absorbent capability.

As can be seen from the results in the example 1, the absorption and retention of a napkin containing coformed material is substantially increased by the presence of microfibers.

EXAMPLE 1

Napkins were made according to the construction depicted in FIG. 4. The only difference was that there were two layers of coformed material each containing 70% meltblown polypropylene and 30% wood pulp fluff for each of three examples. The table below indicates the results of the folded napkin without and with microfiber of this invention. As a comparison, a napkin having two layers of coformed absorbent batts was prepared with a commercially available superabsorbent material. Pads of the composition indicated below were made and they were worn until they failed. These pads were weighed and fluid uptake measured in each layer by weight differential. The results also appear in the table below.

TABLE 1

FLUID DISTRIBUTION IN PADS WITH AND WITHOUT MELTBLOWN MICROFIBERS[A]

| Pad Description | Absorbent Layer Material | Wt., g. | % Fluid Distribution In Each Layer (Menstrual Fluid) |
|---|---|---|---|
| Coform with | Top-Coform | 3.1 | 19 |
| Meltblown Microfiber | MBMF | 2.1 | 61 |
|  | Bottom-Coform | 3.0 | 20 |
| Coform with | Top-Coform | 3.0 | 48 |
| Superabsorbent | Aqausorb | 0.3 | 5 |
| Sheet (Aquasorb*) | Bottom-Coform | 3.0 | 47 |
| Coform (No | Top-Coform | 3.1 | 50 |
| Absorbent Insert) | Bottom-Coform | 3.0 | 50 |

*Aquasorb is a trademark of Hercules Inc. of Wilmington, Delaware

As can be seen from the example above, the presence of thermoplastic microfiber according to this invention minimizes the level of fluid present at the cover of a sanitary napkin (the cover in this instance being spunbonded polypropylene as used conventionally in KOTEX or NEW FREEDOM sanitary napkins). The microfibrous web also, surprisingly, absorbs and retains the majority of the fluid absorbed by this particular napkin configuration.

The utilization of this thin layer of microfibrous web also enables a sanitary napkin having reduced thickness to be made with absorbency comparable to conventional napkin constructions. The embodiments depicted at FIGS. 4 and 5 are particularly adapted to such a napkin. In this instance, napkins having a thickness of between 5 to 15 mm can be made in which the absorbency is comparable to that of the conventional heavy flow napkins now commercially available.

With the teachings of the subject invention in mind, alternative embodiments will readily suggest themselves to those with skill in the art.

What is claimed is:

1. An absorbent pad containing a nonwoven thermoplastic surfactant-treated filamentary microfibrous web, a fluid pervious cover and an absorbent component between said baffle and said cover, said microfibrous web forming at least part of said absorbent component.

2. A sanitary napkin containing a fluid permeable cover, a fluid impervious baffle and an absorbent component said absorbent component including a nonwoven thermoplastic surfactant-treated filamentary microfibrous web.

3. The napkin according to claim 2 wherein the web is treated with a medically safe surfactant.

4. A sanitary napkin according to claims 2 or 6 wherein the microfibrous web terminates prior to the transverse ends of the pad.

5. A sanitary napkin according to claims 2 or 4 wherein a layer of resilient material having lower capillary attraction than said microfibers is positioned between the cover and the microfibrous web and an absorbent layer is positioned between the microfibrous web and the baffle.

6. A sanitary napkin according to claim 2 wherein the napkin has a layer of air-laid wood pulp fluff and polymeric thermoplastic microfibers as part of the absorbent.

7. A sanitary napkin according to claim 2 having folded longitudinal edges.

8. A sanitary napkin according to claims 2, 6 or 7 wherein the microfibrous web is coterminous with the absorbent layer.

9. a sanitary napkin according to claim 2 wherein the thickness of the absorbent layer is between 5 and 15 mm.

10. The sanitary napkin according to claim 8 wherein the sanitary napkin is a panty liner.

* * * * *

UNITED STATES PATENT AND TRADEMARK OFFICE
CERTIFICATE OF CORRECTION

PATENT NO. : 4,372,312
DATED : February 8, 1982
INVENTOR(S) : E. J. Fendler, et al It is certified that error appears in the above—identified patent and that said Letters Patent are hereby corrected as shown below:

At Claim 1, line 3, after "cover" insert -- a fluid impervious baffle --.

Signed and Sealed this

Twenty-third Day of October 1984

[SEAL]

Attest:

Attesting Officer

GERALD J. MOSSINGHOFF

Commissioner of Patents and Trademarks